(12) United States Patent
Haas et al.

(10) Patent No.: US 6,906,014 B2
(45) Date of Patent: Jun. 14, 2005

(54) STABILIZED TOPICAL COMPOSITION

(75) Inventors: Hans E. Haas, Stow, OH (US); Marcia Snyder, Stow, OH (US); Aija Zirnis, Solon, OH (US)

(73) Assignee: Permatex, Inc., Solon, OH (US)

( * ) Notice: Subject to any disclaimer, the term of this patent is extended or adjusted under 35 U.S.C. 154(b) by 0 days.

(21) Appl. No.: 10/238,672

(22) Filed: Sep. 10, 2002

(65) Prior Publication Data

US 2004/0048756 A1 Mar. 11, 2004

(51) Int. Cl.$^7$ ............... C11D 1/66; C11D 3/02; C11D 3/37; C11D 3/43; A61K 7/00
(52) U.S. Cl. ............... 510/130; 510/157; 510/158; 510/159; 510/421; 510/433; 510/434; 510/473; 510/475; 510/477; 510/507; 424/401; 424/70.16; 424/70.31; 424/78.02; 424/78.03
(58) Field of Search ............... 510/130, 157, 510/158, 159, 421, 433, 434, 473, 475, 477, 507; 424/401, 70.16, 70.31, 78.02, 78.03

(56) References Cited

U.S. PATENT DOCUMENTS

| | | | |
|---|---|---|---|
| 4,226,736 A | 10/1980 | Bush et al. | 252/135 |
| 4,648,987 A | 3/1987 | Smith et al. | 252/559 |
| 4,806,262 A | 2/1989 | Snyder | 252/90 |
| 4,992,476 A | 2/1991 | Geria | 514/782 |
| 5,008,030 A | 4/1991 | Cook et al. | 252/106 |
| 5,011,681 A * | 4/1991 | Ciotti et al. | 510/136 |
| 5,393,454 A | 2/1995 | Mondin et al. | 252/174.23 |
| 5,585,104 A * | 12/1996 | Ha et al. | 424/401 |
| 5,683,971 A | 11/1997 | Rose et al. | 510/130 |
| 5,916,967 A | 6/1999 | Jones et al. | 524/732 |
| 5,980,924 A | 11/1999 | Yamazaki et al. | 424/402 |
| 6,191,083 B1 | 2/2001 | Brooks et al. | 510/124 |
| 6,384,010 B1 | 5/2002 | Wagers | 510/470 |
| 6,387,383 B1 * | 5/2002 | Dow et al. | 424/401 |
| 6,440,437 B1 | 8/2002 | Krzysik et al. | 424/402 |

FOREIGN PATENT DOCUMENTS

| | | |
|---|---|---|
| EP | 0 437 956 A1 | 7/1991 |
| EP | 0 586 234 A2 | 3/1994 |
| EP | 0 870 496 A2 | 10/1998 |
| WO | WO 95/03781 | 2/1995 |
| WO | WO 95/05145 | 2/1995 |
| WO | WO 96/32092 | 10/1996 |
| WO | WO 98/23713 | 6/1998 |

OTHER PUBLICATIONS

Japanese Patent Abstract 06016523 A, Jan. 25, 1994.
Japanese Patent Abstract 06056448 A, Mar. 1, 1994.
Japanese Patent Abstract 00191438, Jul. 11, 2000.
Esp@cenet database abstract of WO 98/00499, Jan. 8, 1998.
Nerac abstract of WO 98/00495, Jan. 8, 1998.

* cited by examiner

*Primary Examiner*—Brian P. Mruk
(74) *Attorney, Agent, or Firm*—Gifford, Krass, Groh, Sprinkle, Anderson & Citkowski, P.C.

(57) ABSTRACT

A topical composition has from 0.1 to 2 total weight percent of a first surfactant, an organic solvent, a polymer thickener, and 80 to 98 total weight percent water. The topical composition affords good topical cleaning or lotion actions and rapid water rinse in a form that has a suitable shelf life. The surfactant is chosen to yield a net HLB of between 7 and 13.

37 Claims, No Drawings

STABILIZED TOPICAL COMPOSITION

FIELD OF THE INVENTION

The present invention relates in general to a cleaning composition and, more particularly, to a stabilized waterless cleaning composition.

BACKGROUND OF THE INVENTION

Conventional waterless cleaning compositions contain as much as 45% by weight organic solvents and as much as about 7 weight percent of emulsifiers in order to solubilize grease or soil. These compositions require high concentrations of organic solvents and emulsifiers to remove hydrophobic materials through dual actions of emulsification and solvation. These conventional cleaning compositions have fallen out of favor owing to the high percentage of solvents and emulsifiers that end up in wastewater, as well as the skin irritation associated with the use of such products. The high concentration of organic solvents and emulsifiers makes subsequent removal difficult, often resulting in a residual film that retains soil and/or grease while the film tends to dry and irritate the underlying dermis.

Previous attempts to form a cleaning composition that uses lower percentages of solvents and emulsifiers have met with limited success. Cleaning compositions with low hydrophilic lipophilic balance (HLB) emulsifiers tend to have excellent degreasing properties yet are difficult to remove with aqueous washing. Alternatively, oil and water emulsions formed with high HLB value emulsifiers tend to have lower percentages of organic solvents and are readily rinsed off of a surface with an aqueous wash yet provide poor grease removal. Cleansing compositions with intermediate HLB value emulsifiers tend to have acceptable cleansing and aqueous rinsing properties yet suffer phase separation upon storage. Previous attempts to stabilize intermediate HLB value emulsifiers have resorted to complex combinations of expensive and enviromentally disfavored surfactants. Alternatively, high loadings of thickeners and/or specifically tailored organic solvents have been used. A further complication in providing a cleaning composition based upon an intermediate HLB value emulsifier is that often emulsion stabilizers also function as co-emulsifiers thereby shifting the resulting cleaning composition from the desired intermediate HLB value range that provides effective degreasing and aqueous rinse properties.

In addition to cleaning compositions, skin moisturizing lotions have traditionally included 8–12 weight percent organic solvents and 3–4 weight percent emulsifiers. A lotion is intended to retain water in contact with skin yet avoid a greasy skin sensation. For a lotion, degreasing properties are less important than aqueous rinsing ability and therefore lotions tend to contain higher HLB value emulsifiers, as compared to cleaning compositions. A higher composition HLB value tends to provide a lighter, clean sensation on applied skin. Prior art attempts to reduce the amount of organic solvents and emulsifiers and lotions also have met with limited success.

In view of the state of the art, there exists a need for a cleaning composition containing reduced percentages of organic solvent and emulsifiers. There also exists a need for a lotion or cleaning composition containing an intermediate HLB value emulsifier having acceptable degreasing and aqueous rinsing properties, while maintaining a suitable shelf life.

SUMMARY OF THE INVENTION

DETAILED DESCRIPTION OF THE PREFERRED EMBODIMENTS

An inventive topical composition is a predominantly aqueous formulation for removing a variety of soils and greases from the skin. While the present invention is discussed in the context of a skin cleaning composition, it is appreciated that inventive compositions also have utility as skin lotions, and thickened industrial part degreasers.

The inventive composition also is operative as a waterless hand cleaner. The term "waterless hand cleaner" is defined to include a composition that removes soil and/or grease from the hands of a user absent the addition of water during the hand cleansing process even though water is optionally used thereafter as a rinsing agent.

The present invention is a stabilized high efficiency topical emulsion preferably containing 2–8 total weight percent of organic solvent and 0.05–2 total weight percent of an emulsifier along with a stabilizer. The surprising result of the present invention is a composition that balances a commercially acceptable shelf life of several months, good cleaning and rinsing properties, all in the presence of reduced levels of solvent and emulsifier relative to the prior art. The less expensive and more environmentally friendly inventive composition includes from 80–98% by weight water.

An organic solvent operative in the present invention is capable of solubilizing lipophilic greases and soils. An organic solvent operative herein illustratively includes straight chain or branched chain aliphatic hydrocarbons having from about 6 to about 24 carbon atoms, alkalene glycol, alkalene glycol ether, dibasic ester, and alkyl substituted aromatics. Specific examples of operative organic solvents illustratively include kerosene, naphtha, petroleum distillate, toluene, d-limonene, phenoxyethanol, octanol, methyl soyate, cetyl acetate, and acetylated lanolin alcohol. Preferably, the organic solvent is aliphatic petroleum distillate (CAS 8052-41-3). The concentration of the organic solvent in the cleaning composition is from 1–8 weight percent. More preferably, the organic solvent is present from 2–6 total weight percent.

As used herein, the terms "emulsifier" and "surfactant" are used synonymously. An emulsifier operative herein is a water soluble or water dispersible nonionic or ionic surfactant.

Nonionic emulsifiers representatively include condensation products of an organic, aliphatic or alkyl aromatic hydrophobic compound and ethylene oxide; or alternatively, the hydrophobic compound is condensed with a polyalkylene glycol. It is appreciated that the relative ratio of ethylene oxide or polyethylene glycol to hydrophobic organic, aliphatic or alkyl aromatic is adjustable to modify the HLB value of the resulting emulsifier.

Particularly suitable nonionic emulsifiers having condensation products of aliphatic substituted phenols having aliphatic substituents including from 6–24 carbon atoms and straight or branched chain configurations. The aliphatic substituted phenols condensed with 1–10 moles of ethylene oxide. Preferably, 2–6 moles of ethylene oxide. Specific preferred compounds include n-molar ethoxylated nonylphenol also denoted a nonoxynol-n where n is a rational number between 2.5 and 15. Such nonionic emulsifiers are available from Huntsman Chemical (Salt Lake City, Utah).

Another suitable class of nonionic emulsifiers includes alkoxylated aliphatic alcohols where the base alcohol contains from 6–24 carbon atoms in straight or branched chain configuration. Typically 2–24 moles of ethylene oxide is condensed with the base alcohol. Preferably, 4–8 moles of ethylene oxide is condensed with the base alcohol to form the alkanol ethoxylate. It is appreciated that suitable nonionic emulsifiers are also prepared with the substitution of propylene oxide or a butylene oxide for some or all of the ethylene oxide in the condensation with aliphatic alcohols or alkyl aromatics as detailed herein. Still other derivatives of aliphatics containing 6–24 carbon atoms combined through a sulfur linkage to aliphatic, polyalkene glycol, or alkyl substituted aromatic groups are thioether; glyceride esters that are aliphatic, polyalkene glycol or alkyl substituted aromatic derivatives of glycerides; and ethoxylated alkyl mercaptans where the base thiol contains from 6–24 carbon atoms in straight or branched configuration with 4–24 moles of ethylene oxide; and mono- and di-$C_2$ or $C_3$ amides illustratively including acetamide-, cocamide-, lauramide-, lactamide-, oleamide-, palm kernel amide-, stearamide-, isostearamide-, soyamide-, tallamide-, mono- or di-alkyl amines.

Anionic emulsifiers operative herein include triethanol amine (TEA) salts of $C_{12}$–$C_{60}$ fatty acids, alkyl- and aryl-sulphatic, sulfonic, phosphoric, and phosphonic acids. Specific examples of operative anionic emulsifiers include TEA-stearate, -oleate, -stearate, and -tallate. The anionic emulsifiers operative herein are those characterized by an HLB value from 8 to 13, and preferably from 9 to 12.

Cationic emulsifiers operative herein include quaternary amines, amine oxides and amines. Specific examples of operative quasi cationic emulsifiers include Jeetox C-2 (Jeen International Corp., Fairfield, N.J.).

An emulsifier is present in an inventive composition from 0.05–2 total weight percent of the composition. Preferably, a nonionic emulsifier is present from 0.3–1 total weight percent of the inventive composition. It is appreciated that two or more emulsifiers are optionally utilized in an inventive composition so long as the total amount of emulsifier present in the composition remains below 2 total weight percent. The presence of a second emulsifier is often helpful in adjusting the inventive composition HLB value.

Owing to the small percentage of organic solvent and emulsifier present in the inventive composition, a stabilizer is provided that lacks surfactancy yet provides improved shelf- and stress-stability. The stabilizer includes a polymeric thickener, an inorganic particulate dispersant or a combination thereof.

A polymeric thickener as used in the inventive composition is typically present from 0.1 to 5 total weight percent. Preferably, the polymeric thickener is present from 0.3 to 3 total weight percent. Most preferably the polymeric thickener is present from 0.6 to 1.6 total weight percent of the composition. A polymeric thickener operative herein illustratively includes guar, xanthan, and carregeenan gums; anionic, nonionic, cationic and lipophilically modified guar gums having a molecular weight of from 1,000–1,000,000; polyacrylic acids, polymethacrylic acids, cellulose resins, polyethylene glycols, hydroxy alkyl celluloses, carboxy alkyl celluloses, polyalkylene amines, such as polyethylene amine, starches, modified starches; salts thereof; and combinations thereof each having molecular weights ranging from about 1,000–4,000,000. A particularly preferred polymeric thickener is polyacrylic acid. A polyacrylic acid operative herein is commercially available from Noveon Inc., Brecksville, Ohio under the trade name Carbopol® 934 which is characterized by a viscosity at 0.2% in aqueous solution of between 2,050 and 5,450 milliPascal seconds.

In the event the polymeric thickener or other composition ingredient is excessively acidic, a neutralizing agent is included in order to attain a composition pH of between 5.5 and 9.5. Preferably, final composition pH is between 6.8 and 8.7. A neutralizer operative herein illustratively includes sodium hydroxide, potassium hydroxide, ammonium hydroxide, monoethanolamine, diethanolamine, triethanolamine, and aminomethyl propanol. A preferred neutralizer is triethanolamine. While the quantity of neutralizer present is dictated by the identity of polymeric thickener and the desired composition pH. Typically, a neutralizer is present from 0.02 to 3 total weight percent.

The inventive combination also is stabilized by the addition of an inorganic dispersant. Inorganic dispersant operative as a stabilizer includes fumed silica having an average particle size of 0.01–10 microns. Preferably, the average particle size is between 0.1 and 0.3 microns with the particles being agglomerated to yield a surface area of greater than 25 meters$^2$ per gram. Preferably, the fumed silica surface area is greater than 150 meters$^2$ per gram. Fumed silica, when present, amounts to between 0.1 and 5 total weight percent. Preferably, the fumed silica is present from 0.5 and 3 total weight percent. Other inorganic dispersants include clays such as bentonite, hectorite and smectite, or combinations thereof. When a clay is present as a stabilizer, it is present from 0.1 and 5 total weight percent. Preferably, the clay is present from 0.5 and 3 total weight percent. A specific example of a clay operative in the present composition is a purified smectite clay predominantly containing magnesium aluminum silicate sold under the trade name Veegum® Ultra by RT Vanderbilt Co., Norwalk, Conn. and having an average platelet size of 1×200 nanometer.

An inventive composition is composed primarily of water present from 80 total weight percent to about 99 total weight percent. The HLB value of the inventive composition with the addition of water is between 5.6 and 13. Preferably, the inventive composition HLB value is between 8 and 12. The HLB value calculated as detailed in Remington's Pharmaceutical Sciences, 17$^{th}$ Edition (Mack Publishing Company). It is appreciated that so long as the inventive composition remains within the stated HLB value range. As such, optional ingredients illustratively include an additional anionic surfactant, a cationic surfactant, an amphoteric surfactant, a biocide, an abrasive, an anti-acne agent, an antioxidant, a chelating agent, a colorant, a cosmetic astringent, a topical analgesic, a fragrance, a preservative, an aerosol propellant, an emollient, a humectant, and a sunscreen. Specific ingredients applying to each of these various classes of optional additives are found in the CTFA International Cosmetic Ingredient Dictionary, 6$^{th}$ Edition, 1995.

A preferred optional ingredient is a biocide present from about 0.005–1 total weight percent, the specific amount dictated by the identity and activity of the specific biocide. Biocides operative herein illustratively include those antimicrobial agents recited in U.S. Pat. No. 6,287,583 B1.

Another optional ingredient is an abrasive. An abrasive is typically in the form of a grit operating as a mechanical exfoliant. Operative abrasive grits illustratively include pumice, perlite, polyethylene beads, ground fruit pits or shells, ground luffa fibers, sawdust and other particulate or fibrous materials of synthetic or natural origin. The abrasive grit being typically present from 0.5 to 15 total weight percent. Preferably, the abrasive is present from 2 to 10 total weight percent.

The present invention is further detailed with reference to the following illustrative examples. These examples are intended to illustrate various aspects of the present invention and are not intended to limit the scope of the appended claims.

EXAMPLE 1

A mixing chamber was charged with 30.6 grams of petroleum distillates, 1.6 grams of Surfonic® N-60 (6 mol ethoxylated nonylphenol), 1.6 grams of Igepal® CO 430 (4-mol ethoxylated nonylphenol). A slurry of 2.8 grams of smectic clay (Veegum® Ultra granules, R.T. Vanderbilt Co.), 2.8 grams of polyacrylic acid (Carbomer® 934, Noveon Inc., Brecksville, Ohio), and 0.06 grams of 50% 2 methyl-4-isothiozoline-3-one 50% by weight in propylene glycol (Neolone® M-50 microbiocide, Rohm & Haas, Philadelphia, Pa.) in 335.6 grams of deionized water is prepared. The above ingredients are mixed and homogenized. Separately, 4 grams of triethanol amine are dissolved in 20 grams of deionized water and added with agitation to the main portion. A white opaque uniform gel results. The resulting composition is applied over a 10 mil thick coating of asphalt on polyethylene board. Additionally, an asphalt solution is applied to hands, allowed to dry. The composition applied and the time needed to liquefy and remove the asphalt by hand wringing is recorded. The time for asphalt removal from the board and skin is then measured. Subsequently, the rinsing characteristics after asphalt removal are noted. The above composition successfully removed asphalt from both substrates within 22 seconds and produced a passing skin squeak within 23 seconds of rinsing. The formulation was then subjected to three freeze-thaw cycles with no change in composition stability or performance. The sample is then retained at a temperature of 50° C. for eight weeks with no change in composition stability or performance.

EXAMPLES 2–3

The composition of Example 1 is reformulated with the exception of 6% petroleum distillates, 90.8% water (Example 2) and 5% petroleum distillate, 91.8% water (Example 3). The compositions of Example 2 and Example 3 provided asphalt removal within 12 and 19 seconds, respectively. The rinsing and stability characteristics being comparable to those detailed in Example 1.

EXAMPLES 4–17

The following total weight percentages are prepared and tested as to the removal of 10 mil thick asphalt from substrates as detailed above with respect to Example 1. Unless otherwise noted in Table 1, other component weight percentages are those of Example 3.

EXAMPLES 18–38

Various formulations according to the present invention are provided as total weight percentages in Table 2 along with asphalt removal and rinsing properties thereof. The remainder of the composition being water. Unless otherwise noted, the HLB value of a given example is 9.9 and the pH is 6.8. All formulations shown in Table 2, with the exception of Examples 35 and 36, yielded a "squeaky clean" feel within 20 seconds of rinsing.

EXAMPLE 39

20 grams of mixed cetyl acetate and acetylated lanolin alcohol, sold under the trade name Crodalan LA by Croda Inc. (Parsippany, N.J.) was combined with 10 grams isosteareth-2-octanoate, 10 grams ditrimethylolpropane tetraisostearate, 10 grams octyldodeceth-20 stearate and 5 grams of PEG-20 almond glycerides. The mixture was warmed to 60° Celsius. A thickener phase was produced by combining 920 grams water, 7 grams smectite clay, 7 grams polyacrylic acid (Carbomer® 934), 0.15 grams Neolone® M-50. One-quarter by weight of the thickener phase is warmed to 60° Celsius and added to the oil phase with vigorous agitation. 0.5 grams of fragrance is then added followed by the remaining three-quarters of the thickener phase. 10 grams of triethanolamine is then added and the composition agitated until homogenous. The composition is then provided to a study group of 21 participants (9 female, 12 male) for evaluation as a skin lotion. Each participant is provided with between 1 and 1.8 grams of lotion depending on hand size. Each participant is asked to evaluate spreadability, drag, tackiness, dry time and dry feel of the skin lotion composition. Of the participants, 12 are regular users of dry skin lotions who preferred the skin lotion composition relative to the commercial skin lotion product they currently use. Five other participants, with dry skin who do not regularly use skin lotions, scored the skin lotion composition as favorable especially since the inventive skin lotion composition dried quickly and did not leave a slippery after feel. Four participants, with normal skin oiliness and who only use skincare products occasionally in cold weather, also scored the product favorably. These four participants indicated that they would be amenable to subsequent use of the inventive skin lotion composition. None of the 21 participants asked to evaluate the composition scored the product unfavorably with respect to any of the evaluation criteria.

COMPARATIVE EXAMPLE A

In order to assess the relative cleaning ability of inventive compositions, the comparative removal time is contrasted with that of a control composition. Control composition A includes 27 total weight percent dibasic esters, 1.4% of nonionic emulsifier, 7.5% pumice, with the remainder being inactive thickeners, inactive additives and water. The dibasic esters are by weight 66% dimethyl glutarate, 17% dimethyl adipate and 16.5% dimethyl succinate sold by DuPont Chemicals, Wilmington, Del. under the trade name DBE. The removal substance removal time on a board and rinsing properties are summarized in Table 3. All formulations shown in Table 3 yielded a "squeaky clean" feel within 20 seconds of rinsing.

COMPARATIVE EXAMPLE B

In order to assess the relative cleaning ability of inventive compositions, the comparative removal time of the Example 3 composition is contrasted with that of a control composition. Control composition B includes 37 total weight percent mineral spirits, 8% sodium and ammonium salts of Tall oil acid, 5% nonionic surfactant, 2% mineral oil, and 47.8% water. The removal time of asphalt from a board is 22 seconds for the Example 3 composition and incomplete removal occurred in 2 minutes for Comparative Example B. Triplicate test skin cleaning times are 34 and 110 seconds respectively for Example 3 and Comparative Example B.

TABLE 1

Variations in solvent and emulsifier levels and emulsifier HLB. Effect on cleaning and rinse.

| Example | HLB | Marsol % | Emulsifier A | Amount % | Emulsifier B | Amount % | Removal Asphalt on Board | Removal Asphalt on Skin | Rinsing* | Batch Appearance |
|---|---|---|---|---|---|---|---|---|---|---|
| 4 | calc. 9.7 | 5.0 | Nonoxynol-6 | 0.35 | Nonoxynol-4 | 0.45 | 16 sec. | 8 sec. | Good | Uniform |
| 5 | calc. 10.0 | 5.0 | Nonoxynol-6 | 0.45 | Nonoxynol-4 | 0.35 | 16 sec. | | Good | Uniform |
| 6 | calc. 10.1 | 5.0 | Nonoxynol-6 | 0.5 | Nonoxynol-4 | 0.3 | 19 sec. | | Good | Uniform |
| 7 | 9.9 | 2.5 | Nonoxynol-6 | 0.4 | Nonoxynol-4 | 0.4 | 56 sec. | 21 sec. | Good | Uniform |
| 8 | 9.9 | 1.0 | Nonoxynol-6 | 0.4 | Nonoxynol-4 | 0.4 | 80% in 10 min. | 75 sec. | Good | Uniform |
| 9 | 9.9 | 5.0 | Nonoxynol-6 | 0.2 | Nonoxynol-4 | 0.2 | 31 sec. | 9 sec. | Very Good | Uniform |
| 10 | 9.9 | 5.0 | Nonoxynol-6 | 0.1 | Nonoxynol-4 | 0.1 | 28 sec. | 14 sec. | Excellent | Uniform |
| 11 | 9.9 | 2.5 | Nonoxynol-6 | 0.15 | Nonoxynol-4 | 0.15 | 2 min. 10 sec. | 32 sec. | Good | Uniform |
| 12 | 9.9 | 1.0 | Nonoxynol-6 | 0.1 | Nonoxynol-4 | 0.1 | 5% in 10 min. | 8 min. 30 sec. | Good | Uniform |
| 13 | 9.0 | 5.0 | Nonoxynol-3 | 0.4 | Nonoxynol-9 | 0.4 | 6 sec. | 5 sec. | Good | Uniform |
| 14 | 10.9 | 5.0 | Nonoxynol-6 | 0.8 | — | — | 58 sec. | 38 sec. | Good | Uniform |
| 15 | 8.8 | 5.0 | Nonoxynol-4 | 0.8 | — | — | 7 sec. | 6 sec. | Slow | Translucent |
| 16 | 12.2 | 5.0 | Nonoxynol-8 | 0.8 | — | — | 20% in 10 min. | 6 min. 10 sec. | Excellent | Uniform |
| 17 | 10.0 | 5.0 | Nonoxynol-5 | 0.8 | — | — | 32 sec. | 15 sec. | Good | Uniform |

*Excellent rinsing indicates a "squeaky clean" skin feel within 10 seconds of rinsing. Very Good indicates the same within 15 seconds. Good indicates a clean feel within 20 seconds of rinsing. Slow indicates more than 1 minute of rinsing for a near clean feel. Very Slow indicates that a completely clean feel could not be obtained by rinsing with water.

TABLE 2

| | Organic Solvent‡ | Emulsifier A* | Emulsifier B* | Inorganic Stabilizer** | Polymeric Thickener+ | Other++ | Neutralizer | Note | Asphalt Removal on Board (sec.) |
|---|---|---|---|---|---|---|---|---|---|
| Example 3 | pet. dist. 5% | Nonoxynol-6 0.4% | Nonoxynol-4 0.4% | smectite 0.7% | Carbomer 934 0.7% | | TEA 1.0% | | 22 |
| Example 18 | pet. dist. 5% | Nonoxynol-6 0.4% | Nonoxynol-4 0.4% | smectite 0.7% | Carbomer 934 0.7% | | TEA 3.0% | pH = 8.7 | 24 |
| Example 19 | pet. dist. 5% | Nonoxynol-6 0.4% | Nonoxynol-4 0.4% | smectite 0.3% | Carbomer 934 0.3% | | TEA 1.0% | | 43 |
| Example 20 | pet. dist. 5% | Nonoxynol-6 0.4% | Nonoxynol-4 0.4% | smectite 0.9% | Carbomer 934 0.9% | | TEA 1.0% | | 24 |
| Example 21 | d-limonene 5% | Nonoxynol-6 0.4% | Nonoxynol-4 0.4% | smectite 0.7% | Carbomer 934 0.7% | | TEA 1.0% | | 20 |
| Example 22 | methyl soyate 5% | Nonoxynol-6 0.4% | Nonoxynol-4 0.4% | smectite 0.7% | Carbomer 934 0.7% | | TEA 1.0% | | 32 |
| Example 23 | pet. dist. 5% | trideceth-3 0.8% | — | smectite 0.7% | Carbomer 934 0.7% | | TEA 1.0% | HLB = 7.9 | 42 |
| Example 24 | pet. dist. 5% | thioether 0.8% | — | smectite 0.7% | Carbomer 934 0.7% | | TEA 1.0% | HLB = 11.0 | 14 |
| Example 25 | pet. dist. 5% | Nonoxynol-6 0.4% | Nonoxynol-4 0.4% | smectite 0.7% | Carbomer 934 0.7% | pumice 7.5% | TEA 1.0% | | 9 |
| Example 26 | pet. dist. 5% | Nonoxynol-6 0.4% | Nonoxynol-4 0.4% | smectite 0.7% | Carbomer 934 0.7% | perlite 2.0% | TEA 1.0% | | 8 |
| Example 27 | DBE 5% | thioether 0.5% | — | smectite 0.7% | Carbomer 934 0.7% | pumice 7.5% | TEA 1.0% | | 280 |
| Example 28 | pet. dist. 5% | Nonoxynol-6 0.4% | Nonoxynol-4 0.4% | — | Carbomer 934 1.4% | — | TEA 2.0% | | 12 |
| Example 29 | pet. dist. 5% | Nonoxynol-6 0.4% | Nonoxynol-4 0.4% | — | guar gum 1.4% | — | — | | 11 |
| Example 30 | pet. dist. 5% | Nonoxynol-6 0.4% | Nonoxynol-4 0.4% | — | quaternized guar gum 1.4% | — | — | | 12 |
| Example 31 | pet. dist. 5% | Nonoxynol-6 0.4% | Nonoxynol-4 0.4% | — | NaCMC 1.4% | — | — | | 15 |
| Example 32 | pet. dist. 5% | Nonoxynol-6 0.4% | Nonoxynol-4 0.4% | smectite 0.7% | HEC 1.4% | — | — | | 14 |
| Example 33 | pet. dist. 5% | Nonoxynol-6 0.4% | Nonoxynol-4 0.4% | fumed silica 0.7% | Carbomer 934 0.7% | — | TEA 1.0% | | 18 |
| Example 34 | cetyl acetate 5% | thioether 0.8% | — | smectite 0.7% | Carbomer 934 0.7% | — | TEA 1.0% | HLB = 11 | 17 |
| Example 35 | cetyl acetate 5% | ethoxylated glycerides 0.5% | — | smectite 0.7% | Carbomer 934 0.7% | — | TEA 1.0% | HLB = 10 | 18 |
| Example 36 | decyl | Nonoxynol-2 | thioether 0.4% | smectite 0.7% | Carbomer | — | TEA 1.0% | HLB = 5.6 | 4 |

TABLE 2-continued

| | Organic Solvent‡ | Emulsifier A* | Emulsifier B* | Inorganic Stabilizer** | Polymeric Thickener+ | Other++ | Neutralizer | Note | Asphalt Removal on Board (sec.) |
|---|---|---|---|---|---|---|---|---|---|
| | benzene 5% | 0.4% | | | 934 0.7% | | | | |
| Example 37 | pet. dist. 5% | TEA-tallate 0.6% | — | smectite 0.7% | Carbomer 934 0.7% | — | TEA 1.0% | HLB = 12 | 8 |
| Example 38 | mineral oil 5% | ethoxylated glycerides 0.8% | — | smectite 0.7% | Carbomer 934 0.7% | — | TEA 1.0% | HLB = 10 | 85 |

‡DBE is dibasic acid mixture of 66% dimethyl glutarate, 17% dimethyl adipate, and 16.5% dimethyl succinate available from DuPont Chemicals, Wilmington, DE
*Nonoxynol-n is nonylphenol having n-molar ethoxylation Trideceth-3 is 3 mole ethoxylated tridecanol sold as Rhodasurf BC-420 (Rhodia, Cranbury, NJ)
**Thioether is PEG-6 isolauryl thioether sold under the trade name Alcodat 260 (Rhodia, Cranbury, NJ) Fumed silica is Cabosil MS (Cabot Corp., Tuscola, IL) Ethoxylated glycerides is PEG-20 almond glycerides sold as Crovol A-40 (Croda, Inc., Parsippany, NJ)
+Guar gum is Jaguar HP60 (Rhodia, Cranbury, NJ) Quaternized guar gum is Jaguar C162 (Rhodia, Cranbury, NJ) NaCMC is cellulose gum (Hercules Inc., Wilmington, DE) HEC is hydroxy ethyl cellulose (Hercules Inc., Wilmington, DE)
++Hess grade 0 3/4 (Hess Pumice Products, Inc., Malad, ID) Perlite is Perlite PFF-18 (Pennsylvania Perlite Corp., Bethlehem, PA)

TABLE 3

Comparative Substance Removal

| Substance | Cleaning Composition | Removal Time from Board (sec.) |
|---|---|---|
| Enamel Paint | Comparative Example A | 16 |
| | Example 27 | 72 |
| | Example 34 + 7.5% pumice | 380 |
| Avery ® Permanent Glue Stick | Comparative Example A | 10 |
| | Example 27 | 4 |
| | Example 25 | 7 |
| | Example 34 | 9 |
| Loctite 380 Black Max ® Superglue | Comparative Example A | 9 |
| | Example 27 | 34 |

Patents and publications referenced herein are intended to be incorporated by reference to the full extent as if each individual patent or reference was individually and specifically incorporated herein by reference.

It is understood that the preceding examples are illustrative of the present invention. One skilled in the art will readily appreciate various modifications of the present invention without departing from the spirit thereof. These modifications are intended to fall within the scope of the appended claims.

What is claimed is:

1. A topical composition comprising:
   0.3 to 2 total weight percent of a first surfactant;
   an organic solvent; system consisting of: 2 to 8 total weight percent inclusive of one or more organic solvents;
   a stabilizer selected from the group consisting of: a polymeric thickener, an inorganic dispersant, and combinations thereof; and
   80 to 98 total weight percent water wherein said composition has a net hydrophilic lipophilic balance of between 7 and 9.9.

2. The composition of claim 1 wherein said first surfactant is nonionic.

3. The composition of claim 2 wherein said first nonionic surfactant is present from 0.4 to 0.8 total weight percent.

4. The composition of claim 1 wherein said first surfactant is selected from the group consisting of: alkoxylated aliphatic alcohols, alkoxylated alkyl aromatics, thioethers, glyceride ethers, alkoxylated alkyl mercaptans, mono $C_2$–$C_3$ amino amides, and di $C_2$–$C_3$ amino amides.

5. The composition of claim 1 wherein said first surfactant is a base compound having an alkoxy derivative bonded thereto selected from the group consisting of: a $C_2$–$C_4$ alkoxylated phenol having a $C_6$–$C_{24}$ substituent and $C_2$–$C_4$ alkoxylated $C_6$–$C_{24}$ aliphatic alcohol.

6. The composition of claim 5 wherein the mole ratio of alkoxy derivative to base compound is between 3:1 and 15:1.

7. The composition of claim 5 wherein the mole ratio of alkoxy derivative to base compound is between 4:1 and 9:1.

8. The composition of claim 1 further comprising a second surfactant present in an amount such that said first surfactant and said second surfactant in total are present at less than 2 total weight percent.

9. The composition of claim 8 wherein said second surfactant is selected from the group consisting of: alkoxylated aliphatic alcohols, $C_2$–$C_4$ alkoxylated alkyl aromatics, thioethers, glyceride ethers, $C_2$–$C_4$ alkoxylated alkyl mercaptans, mono $C_2$–$C_3$ amino amides, and di $C_2$–$C_3$ amino amides.

10. The composition of claim 8 wherein said first surfactant and said second surfactant are both nonionic and differ in degree of alkoxylation.

11. The composition of claim 10 wherein said first surfactant and said second surfactant are each independently selected from the group consisting of: a $C_2$–$C_4$ alkoxylated phenol having a $C_6$–$C_{24}$ substituent and a $C_2$–$C_4$ alkoxylated $C_6$–$C_{24}$ aliphatic alcohol.

12. The composition of claim 1 further comprising a neutralizer present in an amount sufficient to raise the pH of said composition to between 5.5 and 9.5.

13. The composition of claim 1 wherein said stabilizer is a combination of said polymeric thickener and said inorganic dispersant.

14. The composition of claim 1 wherein said polymeric thickener is present from 0.1 to 5 total weight percent.

15. The composition of claim 1 wherein said polymeric thickener is selected from the group consisting of: guar, xanthan, and carregeenan gums; anionic, nonionic, cationic and lipophilically modified guar gums having a molecular weight of from 1,000–1,000,000; polyacrylic acids, polymethacrylic acids, cellulose resins, polyethylene glycols, hydroxy alkyl celluloses, carboxy alkyl celluloses, polyalkylene amines; and combinations thereof each having molecular weights ranging from about 1,000–4,000,000.

16. The composition of claim 1 wherein said inorganic disperant is present from 0.1 to 5 total weight percent.

17. The composition of claim 1 wherein said inorganic disperant is selected from the group consisting of: fumed silica and a clay.

18. The composition of claim 1 in the form of a waterless hand cleaner.

19. The composition of claim 1 in the form of a skin lotion.

20. A composition comprising between 0.3 and 2 total weight percent of a first nonionic surfactant; an organic solvent system consisting of: 2 to 8 total weight percent inclusive of one or more organic solvent; a stabilizer selected from the group consisting of polymeric thickener and inorganic dispersant present from 0.1 to 5 total weight percents; and a majority constituent of water wherein said composition has a net hydrophilic lipophilic balance of between 7 and 9.9.

21. The composition of claim 20 wherein said first nonionic surfactant is present from 0.4 to 0.8 total weight percent.

22. The composition of claim 20 wherein said first surfactant is selected from the group consisting of: alkoxylated aliphatic alcohols, alkoxylated alkyl aromatics, thioethers, glyceride ethers, alkoxylated alkyl mercaptans, mono $C_2$–$C_3$ amino amides, and di $C_2$–$C_3$ amino amides.

23. The composition of claim 20 wherein said first surfactant is a base compound having an alkoxy derivative bonded thereto selected from the group consisting of: a $C_2$–$C_4$ alkoxylated phenol having a $C_6$–$C_{24}$ substituent and $C_2$–$C_4$ alkoxylated $C_6$–$C_{24}$ aliphatic alcohol.

24. The composition of claim 23 wherein the mole ratio of alkoxy derivative to base compound is between 3:1 and 15:1.

25. The composition of claim 23 wherein the mole ratio of alkoxy derivative to base compound is between 4:1 and 9:1.

26. The composition of claim 20 further comprising a second nonionic surfactant present in an amount such that said first nonionic surfactant and said second nonionic surfactant in total are present at less than 2 total weight percent.

27. The composition of claim 26 wherein said second surfactant is selected from the group consisting of: alkoxylated aliphatic alcohols, $C_2$–$C_4$ alkoxylated alkyl aromatics, thioethers, glyceride ethers, $C_2$–$C_4$ alkoxylated alkyl mercaptans, mono $C_2$–$C_3$ amino amides, and di $C_2$–$C_3$ amino amides.

28. The composition of claim 20 further comprising a neutralizer present in an amount sufficient to raise the pH of said composition to between 5.6 and 9.5.

29. The composition of claim 20 wherein said stabilizer is a combination of said polymeric thickener and said inorganic dispersant.

30. The composition of claim 20 wherein said polymeric thickener is selected from the group consisting of: guar, xanthan, and carregeenan gums; anionic, nonionic, cationic and lipophilically modified guar gums having a molecular weight of from 1,000–1,000,000; polyacrylic acids, polymethacrylic acids, cellulose resins, polyethylene glycols, hydroxy alkyl celluloses, carboxy alkyl celluloses, polyalkylene amines; and combinations thereof each having molecular weights ranging from about 1,000–4,000,000.

31. The composition of claim 20 wherein said inorganic particulate is selected from the group consisting of: fumed silica and a clay.

32. A process for stabilizing a topical composition having a hydrophilic lipophilic balance of between 7 and 13, an organic solvent system consisting of: 2 to 8 total weight percent inclusive of one or more organic solvents, water and a surfactant therein comprising the steps of:
  adding a polymeric thickener in an amount from 0.1 to 5 total weight percent; and
  dispersing an inorganic particulate in an amount of between 0.1 and 5 total weight percent, said inorganic particulate selected from the group consisting of: fumed silica, bentonite, hectorite, smectite, and combinations thereof.

33. The process of claim 32 further comprising the step of: neutralizing the composition to a pH of between 5.5 and 9.5.

34. The process of claim 32 wherein said polymeric thickener lacks surfactancy in the composition.

35. The process of claim 32 wherein the surfactant is present from 0.1 to 2 total weight percent.

36. The process of claim 32 wherein the surfactant is nonionic.

37. The process of claim 32 wherein said polymeric thickener is selected from the group consisting of: guar, xanthan, and carregeenan gums; anionic, nonionic, cationic and lipophilically modified guar gums having a molecular weight of from 1,000–1,000,000; polyacrylic acids, polymethacrylic acids, cellulose resins, polyethylene glycols, hydroxy alkyl celluloses, carboxy alkyl celluloses, polyalkylene amines; and combinations thereof each having molecular weights ranging from about 1,000–4,000,000.

* * * * *

UNITED STATES PATENT AND TRADEMARK OFFICE
CERTIFICATE OF CORRECTION

PATENT NO.       : 6,906,014 B2
APPLICATION NO. : 10/238672
DATED            : June 14, 2005
INVENTOR(S)      : Hans E. Haas Page 1 of 1

It is certified that error appears in the above-identified patent and that said Letters Patent is hereby corrected as shown below:

Front Page, References Cited - Replace "Ciotti et al.  510/136" with --Cotti et al. 424/81--.

Column 9, line 51 - Replace "organic solvent;" with --organic solvent--.

Column 11, line 14 - Replace "solvent;" with --solvents; --.

Column 11, line 16 - Replace "percents;" with --percent--.

Signed and Sealed this

Twenty-second Day of August, 2006

JON W. DUDAS
*Director of the United States Patent and Trademark Office*